United States Patent [19]

Kielley

[11] Patent Number: 4,970,240

[45] Date of Patent: Nov. 13, 1990

[54] FRUITY FLAVORED NASAL DECONGESTANT COMPOSITION

[75] Inventor: James R. Kielley, Springfield, N.J.

[73] Assignee: Schering Corporation, Kenilworth, N.J.

[21] Appl. No.: 423,075

[22] Filed: Oct. 18, 1989

[51] Int. Cl.$^5$ ................. A61K 9/08; A61K 35/78
[52] U.S. Cl. ................. 514/783; 514/853; 514/854; 514/974
[58] Field of Search ............... 514/783, 853, 854, 974

[56] References Cited

U.S. PATENT DOCUMENTS

| | | | |
|---|---|---|---|
| 4,053,628 | 10/1977 | Stevenson et al. | 514/912 |
| 4,603,131 | 7/1986 | Bernsten et al. | 514/656 |
| 4,639,367 | 1/1987 | Mackles | 514/945 |
| 4,665,095 | 5/1987 | Winn et al. | 514/401 |
| 4,826,683 | 5/1989 | Bates | 514/853 |

*Primary Examiner*—Shep K. Rose
*Attorney, Agent, or Firm*—Thomas D. Hoffman; Gerald S. Rosen; John J. Maitner

[57] ABSTRACT

An aqueous, flavored, topical, nasal decongestant composition containing an amount of oxymetazoline or a pharmaceutically acceptable salt thereof, e.g., oxymetazoline HCl sufficient to effect nasal decongestion and an amount of a fruity flavor e.g. cherry flavor, sufficient to mask the medicinal after-taste of the composition, together with an aqueous carrier.

10 Claims, No Drawings

FRUITY FLAVORED NASAL DECONGESTANT COMPOSITION

BACKGROUND

This invention relates to an aqueous, flavored, topical, nasal decongestant composition containing doxymetazoline or a pharmaceutically acceptable salt thereof, an aqueous carrier and sufficient fruity flavor to mask the medicinal after-taste of the composition.

Aqueous, topical, nasal decongestant compositions containing oxymetazoline hydrochloride, the longest acting nasal decongestant currently available, are applied to the nasal passages of mammals especially human beings to affect temporary relief of nasal congestion associated with colds, hay fever and sinusitis. Menthol flavored nasal decongestant compositions containing vapors of menthol, eucalyptol and camphor and polysorbate in addition to oxymetazoline hydrochloride and an aqueous carrier are available as OTC products under the tradename AFRIN® nasal spray from Schering Corporation, Kenilworth, New Jersey. However, such menthol flavored or unflavored nasal decongestant composition when applied to the nasal passages, causes a bitter medicinal after-taste.

T. M. Berman (New England Journal of Medicine, Aug. 23, 1979, Vol. 301, p 437) discloses addition of peppermint flavor to improve the taste of lidocaine used to anesthetize the pharynx and nasal passage before bronchoscopy. D. E. Hornung et al. (Ann N.Y. Acad. Sci., 1987, Vol. 510, pp 86–90) discloses smell-taste perception in general terms. Neither reference discloses or suggests the present invention.

SUMMARY OF THE INVENTION

We have surprisingly discovered that addition of small amounts of fruity flavors to aqueous topical nasal decongestant compositions containing oxymetazoline hydrochloride in an aqueous base effectively masks the medicinal after-taste of the decongestant composition. Accordingly, the present invention provides an aqueous, flavored, topical nasal, decongestant composition comprising an amount of oxymetazoline or a pharmaceutically acceptable salt thereof sufficient to effect nasal decongestion and an aqueous carrier and an amount of a fruity flavor sufficient to mask the medicinal after-taste of the topical nasal decongestant composition. The present invention also provides an aqueous, flavored, topical nasal decongestant composition comprising an amount of oxymetazoline or a pharmaceutically acceptable salt thereof sufficient to effect nasal decongestion and an aqueous carrier containing:

about 4.0 to about 7.0% by weight of 70% (w/v) sorbitol solution;

about 0 to about 0.025% by weight of at least one antimicrobial preservative;

about 0.005 to about 0.5% by weight of a fruity flavor, and an amount of a pharmaceutically acceptable base and buffer sufficient to maintain the pH of the composition within the range of about 4.0 to about 6.5, and water. The present invention further provides a method of treating nasal congestion by administering to a nasal passage of a patient with nasal congestion an aqueous, fruity-flavored, topical nasal decongestant composition of the present invention.

DETAILED DESCRIPTION OF THE INVENTION

The fruity flavors found suitable for use in the present invention include cherry, strawberry, peach and vanillin all of which are flavors approved for use in drugs by the United States FDA. The amount of fruity flavor found sufficient to mask the medicinal after-taste of the topical nasal decongestant compositions of the present invention is within the range of about 0.005 to about 0.5% by weight of the composition. The ranges for individual fruity flavors are given in the table below.

| Fruity Flavor | Concentration Range | |
| --- | --- | --- |
| | mg/mL | Percent by Weight of Composition |
| Cherry | 0.1–4.0 | 0.0–1 to 0.4 |
| Strawberry | 0.05–5 | 0.005 to 0.5 |
| Peach | 0.1–3 | 0.01 to 0.3 |
| Vanillin | 0.1–3 | 0.01 to 0.3 |

The use of cherry flavor (preferably about 3.5 mg/mL) or strawberry (preferably about 4.0 mg/mL) in the compositions and methods of the present invention is preferred.

The amount of oxymetazoline or pharmaceutically acceptable salt thereof found sufficient to effect nasal decongestion is in the range of about 0.01% to about 0.1% by weight of the topical nasal decongestant composition. Typically, 0.025% by weight oxymetrazoline (as the HCl) is suitable for children 2 to 5 years of age and 0.05% by weight of oxymethazoline (also as the HCl salt) is suitable for adults and children above five years of age. Oxymetazoline HCl is commercially available from Schering Labs, Kenilworth New Jersey. See also The Merck Index, Tenth Edition, 1983 p. 6838. By the term "pharmaceutically acceptable salt" as used herein is meant the acid addition salt formed by admixing oxymetazoline with a pharmaceutically acceptable acid such as HCl, HF, $H_2SO_4$, $HNO_3$, malonic, succinic, trifluoroacetic acids and the like.

The compositions of the present invention contains at least one antimicrobial preservative in the range of 0% to about 0.025% by weight of the composition. Typical suitable preservatives function as antimicrobial agents and include the commercially available preservatives, e.g. phenyl mercuric acetate in the range of about 0 to about 0.005% by weight, benzalkonium chloride in the range of about 0 to about 0.02% by weight or thimerosal in the range of about 0.001 to about 0.01% by weight.

The compositions of the present invention contain a sorbitol solution (70% w/v) normally present in the range of about 4.0 to 7.0% by weight. Sorbitol solution is a tonicity agent which renders the composition of the present invention isotonic with the body's fluids. Other concentrations of sorbitol and other tonicity agents well known to those skilled in the art are contemplated to be within the scope of this invention.

The compositions of the present invention also include pharmaceutically acceptable buffers and pharmaceutically acceptable bases sufficient to adjust and maintain the pH of the compositions of the present invention in the range of about 4.0 to about 6.5, preferably about 5.5 to about 6.5. Typically suitable buffers include citrate, phosphate and glycine. Typically suitable bases include alkali metal hydroxides, especially NaOH.

The compositions of the present invention may be formulated for use by adults or children in the form of nose drops, or spray. A spray pump or plastic squeeze bottle may be use for the spray. The dosage and administration regimen of Schering Corporation AFRIN® nasal spray in the 1988 edition of the PDR for NON-PRESCRIPTION DRUGS at page 685 may be followed.

EXAMPLE 1

Adult Strength Flavored Product

| Ingredient | Concentration mg/mL | % by wgt. |
|---|---|---|
| Oxymetazoline HCl | 0.50 | .05 |
| Phenylmercuric Acetate | 0.02 | .002 |
| Benzalkonium Chloride | 0.20 | .02 |
| Glycine | 3.754 | .3754 |
| 70% (w/v) Sorbitol Solution | 57.143 | 5.7143 |
| Cherry Flavor | 3.5 | .35 |
| Sodium Hydroxide to adjust pH to within range of 5.5 to 6.5 | — | — |
| Water Purified USP | q.s to 1 mL | |

METHOD OF PREPARATION (1) Dissolve the oxymetazoline HCl, phenyl mercuric acetate, benzalkonium chloride, glycine, 70% (w/v) sorbitol solution, and cherry flavor into a volume of purified water sufficient to provide a homogeneous solution. Adjust the pH of the so-formed solution to 5.5 to 6.5 using a sodium hydroxide solution. Add sufficient purified water to the final volume (1 mL) having the ingredient concentrations listed above. Filter the solution.

Strawberry (4 mg/mL) may be substituted for cherry flavor in the above formulation.

Fill into 15 or 30 mL plastic squeeze bottles or 15 mL pump spray bottles or 20 mL dropper bottles.

EXAMPLE 2

Children's Strength Flavored Product

Follow the procedure of Example 1 but use 0.25 mg/mL of oxymetazoline HCl in the formulation instead of 0.50 mg/ml.

EXAMPLE 3

Exemplary Formulations

| Ingredients | Concentration Range mg/mL | % by wgt. |
|---|---|---|
| Oxymetazoline | 0.01–0.1 | 0.001–0.01 |
| Phenylmercuric acetate | 0–0.05 | 0–0.005 |
| Benzalkonium Chloride | 0–0.2 | 0–0.02 |
| 70% (w/v) Sorbitol Solution | 40–70 | 4.0–7.0 |
| Fruity Flavor | 0.05–5 | 0.005–0.5 |
| Buffer and NaOH sufficient to adjust and maintain pH in the range of 5.5 to 6.5 | | |
| Water | q.s to 1 ml | |

The composition of Example 1 in the form of a nasal spray was tested and found to have no medicinal after-taste.

What is claimed is:

1. A method of masking the medicinal after-taste of a nasally-applied oxymetazoline-containing decongestant composition which comprises nasally applying an aqueous, flavored, topical nasal decongestant composition comprising (1) an amount of oxymetazoline or a pharmaceutically acceptable salt thereof sufficient to effect nasal decongestion, (2) an aqueous carrier containing an amount of a fruity flavor sufficient to mask the medicinal after-taste of the topical nasal decongestant composition.

2. The method of claim 1 wherein the fruity flavor is cherry or strawberry.

3. A method of masking the medicinal after-taste of a nasally-applied oxymetazoline-containing decongestant composition which comprises nasally administering an aqueous, flavored, topical, nasal decongestant composition comprising (1) an amount or oxymetazoline of a pharmaceutically acceptable salt thereof sufficient to effect nasal decongestion and (2) an aqueous carrier containing:
  about 4.0 to about 7.0% by weight of sorbitol;
  about 0 to about 0.25% by weight of at least one antimicrobial preservative;
  about 0.005 to about 0.5% by weight of a fruity flavor, and (3) an amount of a pharmaceutically acceptable base and buffer sufficient to maintain the pH of the composition within the range of about 4.0 to about 6.5; and (4) water.

4. The method of claim 3 wherein the oxymetazoline HCl comprises about 0.01 to about 0.1% by weight of the composition.

5. The method of claim 3 wherein the aqueous, flavored, topical, nasal decongestant composition consists essentially of:

| Ingredients | Concentration mg/mL |
|---|---|
| Oxymetazoline HCl | 0.50 |
| Phenylmercuric Acetate | 0.02 |
| Glycine | 3.754 |
| 70% (w/v) Sorbitol Solution | 57.143 |
| Benzalkonium Chloride | 0.20 |
| Fruity Flavor | 0.05 to 5 |
| Sodium Hydroxide to adjust the pH to 5.5 to 6.5 | — |
| Water | q.s to make 1 mL |

6. The method of claim 5 wherein the nasal decongestant contains 3.5 mg/mL of cherry flavor.

7. The method of claim 6 wherein the nasal decongestant contains 4 mg/mL of strawberry flavor.

8. A method of treating nasal congestion which comprises administering to a nasal passage of a patient with nasal congestion an aqueous, flavored, topical, nasal decongestant composition of claim 1.

9. The method of claim 8 wherein said nasal decongestant composition is administered as a spray via a squeeze bottle.

10. The method of claim 8 wherein said nasal decongestant composition is administered as a spray via a spray pump bottle.

* * * * *